(12) United States Patent
Alberts

(10) Patent No.: US 6,537,132 B1
(45) Date of Patent: Mar. 25, 2003

(54) MATERNITY BRACE

(76) Inventor: Gina Alberts, 5 North Villas, London NW1 9BJ (GB)

( * ) Notice: Subject to any disclaimer, the term of this patent is extended or adjusted under 35 U.S.C. 154(b) by 0 days.

(21) Appl. No.: 09/696,873

(22) Filed: Oct. 26, 2000

(51) Int. Cl.[7] .................................................. A41C 1/08
(52) U.S. Cl. ........................................ 450/155; 450/100
(58) Field of Search ............................ 450/155, 94, 95, 450/97, 100–109; 604/385.1, 391, 392, 394, 397; 2/406, 44, 45, 310–312, 338, 92; 602/19; 128/90.1, 96.1, 99.1, 100.1, 101.1

(56) References Cited

U.S. PATENT DOCUMENTS

| | | | |
|---|---|---|---|
| 395,050 A | * 12/1888 | Gray | 450/155 |
| 1,126,765 A | * 2/1915 | Hynds | 450/155 |
| 3,116,736 A | 1/1964 | Alberts | |
| 3,376,864 A | * 4/1968 | Gulack | 450/155 |
| 4,195,640 A | 4/1980 | Castiglia | |
| 5,702,286 A | * 12/1997 | Seering et al. | 450/155 |
| 6,159,070 A | * 12/2000 | Schwartz et al. | 450/155 |

* cited by examiner

Primary Examiner—Gloria M. Hale
(74) Attorney, Agent, or Firm—Schweitzer Cornman Gross & Bondell LLP

(57) ABSTRACT

A maternity brace for providing support to the vulval and abdominal regions of a pregnant woman. The maternity brace has a central vulval panel and a pair of front and rear straps attached thereto. A body-encircling adjusting belt is in communication with the front and rear straps. An abdominal panel positioned between the two front straps applies a supporting force to the abdomen. A back panel along the back of the adjusting belt imparts stability to the lower back. The front and rear straps may be nonlinear to add comfort and support. Wearing the maternity brace improves the overall well-being of an expectant mother and helps to prevent varicose veins, stretch marks, back pain, cystocele, rectocele, hemorrhoids, increased wear on knee and hip joints, reduced blood circulation, and overall fatigue.

20 Claims, 3 Drawing Sheets

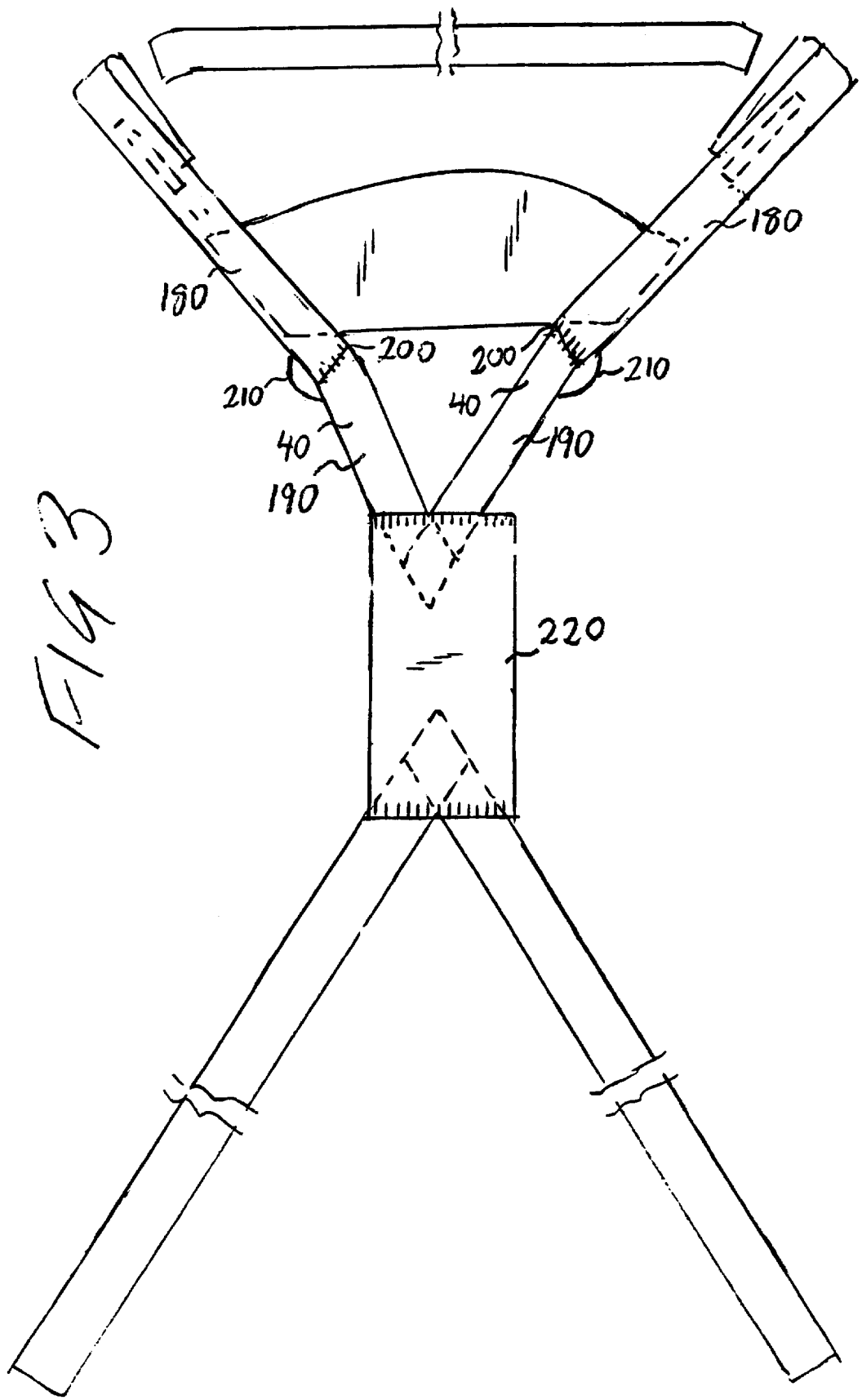

MATERNITY BRACE

FIELD OF THE INVENTION

The present invention relates to a support brace for providing support to the vulval and abdominal regions of a pregnant woman and for reducing or eliminating the deleterious effects of the increased body weight of pregnancy.

BACKGROUND OF THE INVENTION

The additional size and weight of the fetus in a pregnancy often impact negatively on several body parts and the overall well-being of an expectant mother. Varicose veins may develop. Hemorrhoids may form. Conditions such as cystocele and rectocele may occur. The additional weight of the fetus places a strain on the lower back and may cause poor posture and back pain. Knee and hip joints may fatigue from the extra stress. Stretch marks may appear in the abdominal region. Thus there is a need for therapies and other means to alleviate or prevent these conditions.

Various types of supportive garments and girdles have been proposed to help reduce the deleterious effects of both fetal weight and additional body weight of the expectant mother. For example, Alberts U.S. Pat. No. 3,116,736 discloses a body support having both a vulval support for supporting the vulval region of the wearer and a girdle for providing beneficial support to the abdominal region. Castiglia U.S. Pat. No. 4,195,640 discloses a lower torso support appliance having both an inelastic front panel for engaging the abdominal region of the wearer and a rigid sheet-like member for engaging the lower back.

SUMMARY OF THE INVENTION

The maternity brace of the present invention improves on earlier devices of this general type in that it provides considerably more support to the abdomen of the wearer and distributes forces otherwise focused in the abdominal region to other portions of the body. The new maternity brace further provides enhanced support and greater stability to the lower back. It may be adjusted easily to fit wearers regardless of how far along they are into their pregnancies. The new brace is extremely comfortable and very lightweight, and it may be folded and stored in a small bag.

Hereinafter, the term "vertical axis" means an axis which extends longitudinally head-to-toe; the term "transverse axis" means an axis which extends horizontally from the front to the rear of the body. The term "inward" means the direction toward the body from the exterior; the term "outward" means the direction away from the body. The term "upward" means toward the head; the term "downward" means toward the feet.

The maternity brace of the present invention has many improvements over earlier supportive garments. It is fabricated from thinner components to provide a very thin profile, allowing it to remain comparatively inconspicuous beneath clothing. A specially integrated and designed back panel provides stability to the lower back to reduce strain thereon, in turn preventing back pain and improving posture. A specially configured and integrated flexible abdominal panel conforms to and engages the lower abdomen. When in tension, the abdominal panel applies a beneficial supporting force to the abdomen, which force is directed inward along the transverse axis of the body. Moreover, this supporting force is also directed upward along the vertical axis of the body. As a result and in accord with an important principle of the invention, the abdominal panel applies not only an inward force but also a considerable upward force to the abdomen, in turn distributing the downward forces otherwise focused in the abdominal region to other portions of the body. The particular configuration of the maternity brace directs these downward forces to the periphery of the waist, thus shifting the forces to a position closer to the center of gravity of the body in order to reduce pressure on the pelvis, increase blood circulation in the abdominal region, and reduce overall fatigue. The abdominal panel also provides beneficial support to the abdominal region by holding the abdomen more securely in place, resulting in improved posture, reduced wear in the knee and hip joints, and increased mobility for the wearer. The maternity brace is fabricated from materials that are aesthetically attractive and are available in a variety of colors to appeal to fashion conscious wearers.

At the base of the maternity brace of the present invention is a specially configured vulval panel sufficiently wide to embrace the vulval region comfortably without irritating the vagina. The vulval panel engages the labia majora without entering therebetween while providing support to the vulval region. A pair of fabric front straps and a pair of fabric rear straps are attached to the vulval panel. The front and rear straps extend out from the vulval panel, forming an X-configuration which adapts and conforms to the specific anatomy of the wearer. A body-encircling adjusting belt is connected to the front and rear straps for securing the straps and for applying an upward force to the straps when the brace is worn. As a result, tension in each strap causes the straps to apply an upward force to the vulval panel.

The adjusting belt has locking means in its front section for opening and closing the belt to facilitate putting on and removing the maternity brace. The adjusting belt also has an adjustable effective length to accommodate the girths of many different wearers and to adjust the tension in the belt. A mechanical clasp is a preferred locking means. The adjusting belt wraps around the body along the region of the upper abdomen in order to rest securely on the body and anchor the front and rear straps.

Each of the two front straps is long enough to wrap around the front section of the adjusting belt and connect back to itself when the maternity brace is worn. Each of the two rear straps is long enough to wrap around the back section of the adjusting belt, then return to a front strap. The rear straps cross each other along the outward surface of the vulval panel. This crisscross configuration supplements the support to the vulval region. The front and rear straps have adjustable effective lengths to accommodate the anatomy of different users and are stretchable in one dimension (lengthwise) for conforming tightly to the body when the straps are in tension, whether the wearer is walking or standing still.

In a preferred embodiment of the invention, an abdominal panel positioned between the two front straps applies inward and upward supporting forces to the abdomen of the wearer. Thus the abdominal panel helps to distribute downward forces exerted by the fetus in the abdominal region to other portions of the body, effectively shifting those forces to a position closer to the center of gravity of the body. The abdominal panel is fabricated from a flexible material, causing its shape to adapt to the contours of the abdomen. This material has some elasticity and is stretchable in two dimensions to conform tightly to the abdomen. The abdominal panel is removable from the brace, allowing the wearer to use the brace as a vulval support when additional abdominal support is not desired.

The maternity brace advantageously has a back panel positioned along the back section of the body-encircling adjusting belt. The back panel is wider than the adjusting belt and is provided with a lining material, e.g., padding, where it contacts the back of the wearer for enhanced comfort. The back panel helps to stabilize and to ease pressure on the lower back. The back panel is advantageously removably secured to the adjusting belt.

In an alternate preferred embodiment of the invention, each of the two rear straps has upper and lower segments that are angularly displaced from each other. This nonlinearity changes the position of each rear strap on the body of the wearer, resulting in enhanced comfort and increased support. For example, when the rear straps are positioned along the sides of the body, they provide increased lateral support. Similarly, in this embodiment each of the two front straps advantageously has upper and lower segments angularly displaced from each other for added comfort and support.

BRIEF DESCRIPTION OF THE DRAWINGS

FIG. 3 is a top plan view of the maternity brace.

DESCRIPTION OF PREFERRED EMBODIMENTS

Figure 1:
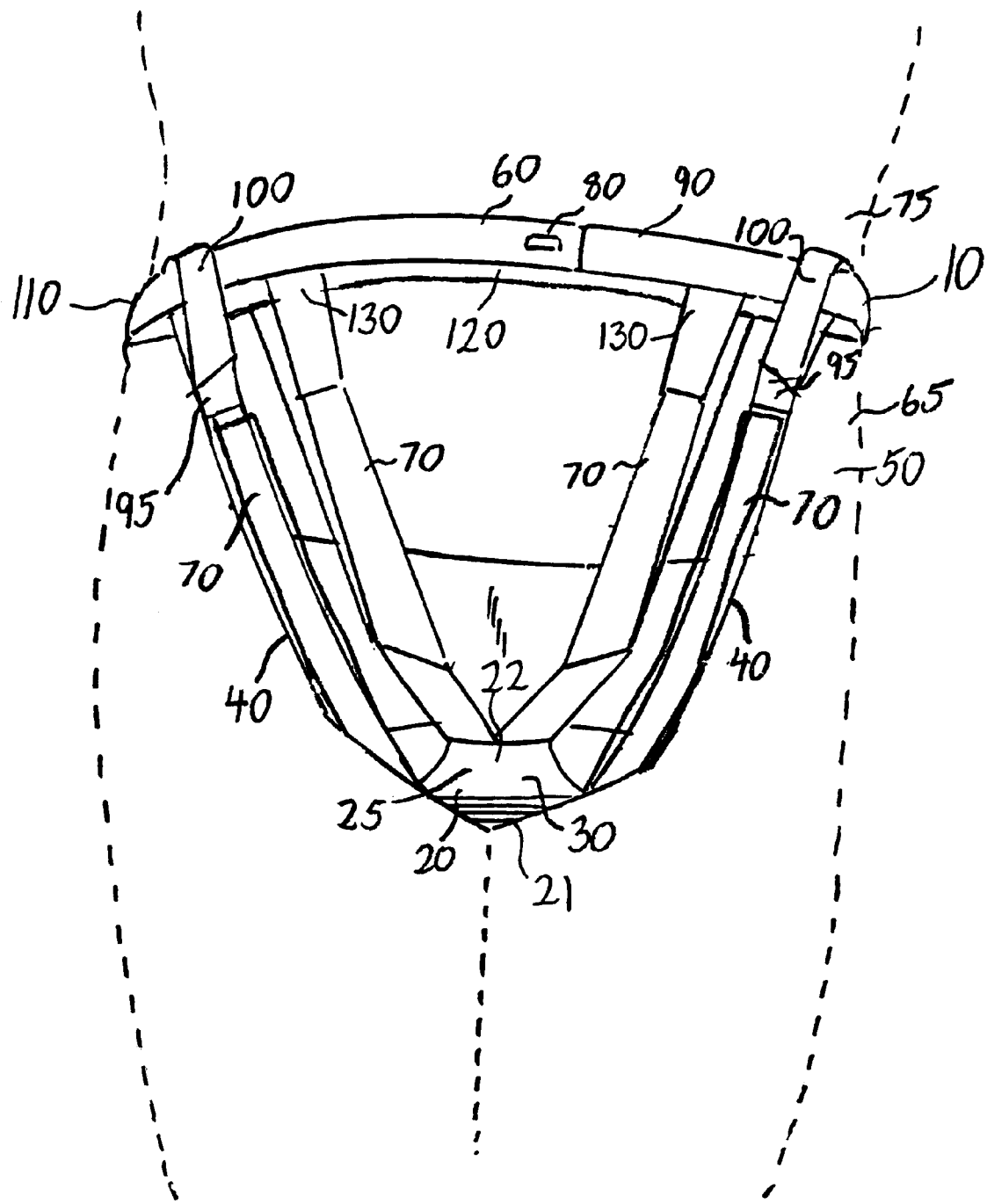
FIG. 1 is a front perspective view of the maternity brace of the present invention being worn by a pregnant woman.

As shown in FIG. 1, the maternity brace 10 of the present invention has a central vulval panel 20 that engages the vulval region 30 of the wearer. The vulval panel 20 embraces the vaginal region without irritating the vagina, for it has a width sufficiently large to prevent it from entering the vagina between the labia majora when applying an upward pressure thereto. The vulval panel 20 may be rectangular or may instead have another shape (e.g., oval). It is flexible and has some elasticity, causing it to conform closely and comfortably to the vulval region of the body. Preferably, the vulval panel is stretchable in only one dimension, specifically lengthwise from the front 21 to the rear 22 of the vulval panel, and has a width between 2 and 4 inches.

A pair of front straps 40 attached to the vulval panel 20 extend upwardly and outwardly along the pelvis 50 of the wearer and attach to a body-encircling adjusting belt 60. A pair of rear straps 70 extend upwardly and outwardly and also attach to the adjusting belt 60. Part of each rear strap 70 superimposes a front strap 40 when the maternity brace is worn. Preferably, the front straps, rear straps, and adjusting belt are stretchable in one dimension (lengthwise), have a width between ¾ and three inches, and have a depth less than ¼ inch.

The adjusting belt 60 wraps around the body along the region of the abdomen 65 of the wearer, preferably the upper abdomen 75. The belt 60 rests securely on the body and applies an upward force to each of the front and rear straps when the maternity brace 10 is worn, creating tension in those straps. The front and rear straps in turn apply an upward force to the vulval panel 20, providing support to the vulval region 30 of the body.

The adjusting belt 60 has locking means 80 in its front section 90 for opening and closing the belt 60 when putting on and removing the brace 10. A mechanical clasp is a preferred locking means 80. Alternately, the locking means may comprise hook and loop fasteners. The effective length of the adjusting belt 60 may be adjusted either by adjusting the position of the locking means along the belt or by adjusting a separate adjustment means, such as a common strap coupling (not shown) positioned along the belt.

Each front strap 40 loops around the adjusting belt 60 in the front section 90 of the adjusting belt (or in one of the side sections 110 of the adjusting belt) and attaches back to itself via attachment means, such as hook and loop fasteners 95. As a result, each front strap 40 forms a front loop 100. Each rear strap 70 loops around the adjusting belt 60 in either a side section 110 or the back section 120 of the adjusting belt 60, forming a rear loop 130. This looping arrangement allows adjustment of the straps along the length of the adjusting belt.

Each rear strap is long enough to wrap around the back section of the adjusting belt, then return to a front strap and lie along the outward surface of the front strap, as shown in FIG. 1. The rear straps 70 cross each other along the outward surface 25 of the vulval panel 20. This criss-cross configuration supplements the support to the vulval region. The front and rear straps have adjustable effective lengths to accommodate the anatomy of different users and to adjust the tension in the straps.

Figure 2:
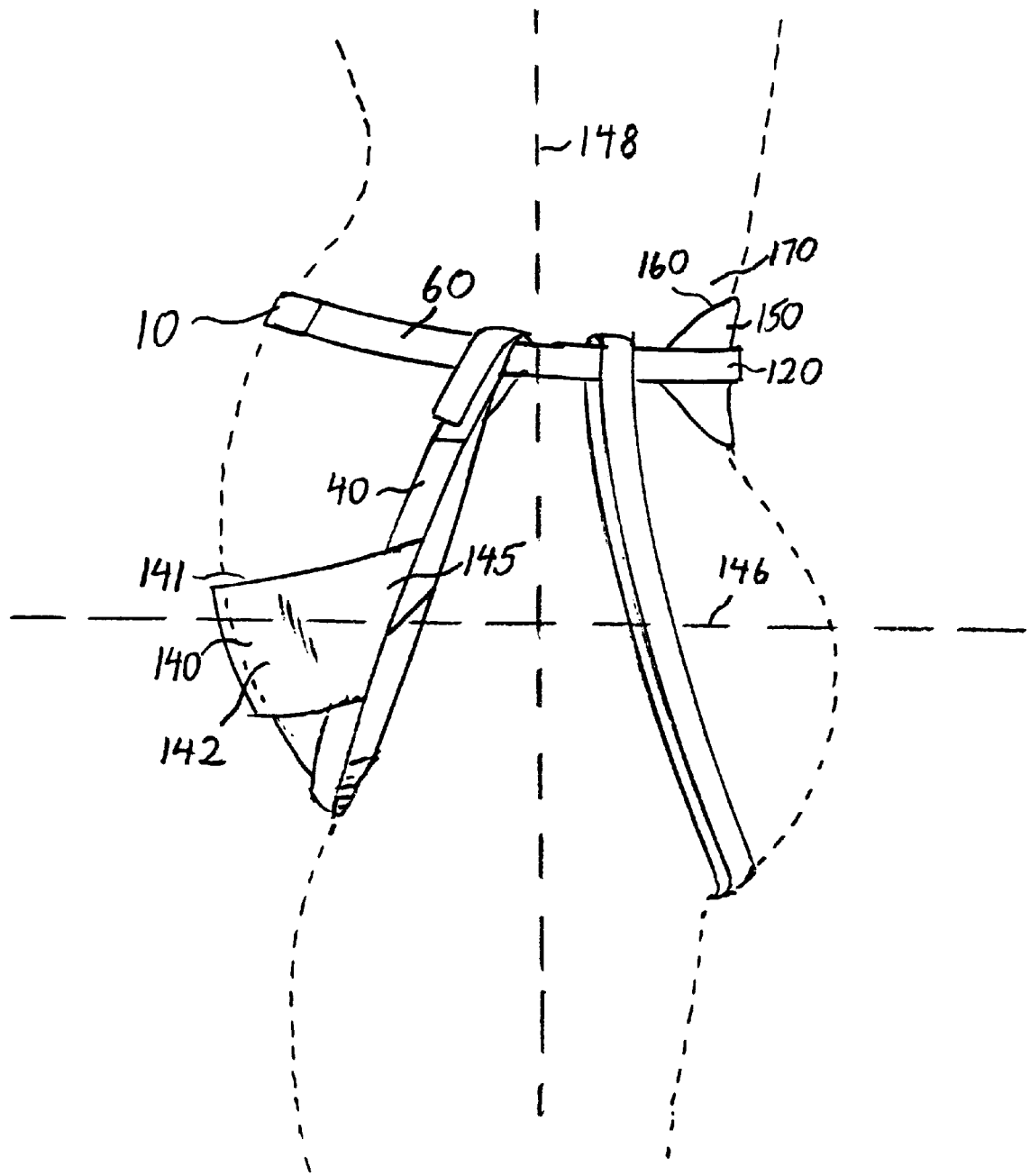
FIG. 2 is a side perspective view of the maternity brace being worn by a pregnant woman.

As shown in FIG. 2, a flexible abdominal panel 140 is positioned between the two front straps 40 (only one front strap is shown in FIG. 2) and is held in place by connection means 145, such as hook and loop fasteners. The connection means 145 allow the wearer to adjust the effective length, as well as the tension, of the abdominal panel 140. The flexible abdominal panel 140 engages the abdomen 141, specifically the lower abdomen 142, of the wearer. When in tension, the abdominal panel 140 applies a supporting force to the lower abdomen 142. The supporting force is directed inward along the transverse axis 146 of the body and upward along the vertical axis 148 of the body. Therefore, the abdominal panel applies not only an inward force but also a considerable upward force to the abdomen, effectively distributing the downward forces otherwise focused in the abdominal region (e.g., those exerted by the fetus) to other portions of the body. In particular, tension in the abdominal panel 140 travels up through the front straps 40 to the adjusting belt 60, which in turn directs the downward forces to the periphery of the waist, thus shifting the downward forces in the abdominal region to a position closer to the center of gravity of the body. The abdominal panel also provides support to the abdominal region by holding the abdomen 141 more securely in place.

The abdominal panel 140 has a convex shape and is fabricated from material which is not only flexible but also stretchable in two dimensions in order to embrace the abdomen more tightly. The connection means 145 allow the wearer to adjust not only the tension and effective length of the abdominal panel 140, but also the position where the abdominal panel connects to each of the front straps 40 and the angle of this connection. Adjusting the angle of connection affects the extent to which the supporting force exerted by the abdominal panel is directed upward as well as inward.

Also shown in FIG. 2, the maternity brace 10 has a back panel 150 positioned along the back section 120 of the adjusting belt 60. The back panel 150 is wider than the adjusting belt and has a lining material 160, e.g., padding, where it contacts the lower back of the wearer. The back panel is preferably oval or rectangular in shape and has sufficient width to impart stability to the lower back 170. The back panel is comparatively rigid but preferably still has some flexibility both to adapt to the contours of the back and to allow movement in the lower back. The back panel 150 has attachment means (hidden), such as hook and loop fasteners, for removably fastening the back panel 150 to the back section 120 of the adjusting belt.

As shown in FIG. 3, the front straps 40 of an alternate preferred embodiment of the maternity brace 220 need not be linear. For example, in this embodiment each front strap has an upper segment 180 and a lower segment 190 joined together at a junction 200 where they form an obtuse angle 210. Each rear strap is shaped similarly (not shown). Alternately, each angle 210 may be greater than 180 degrees, or each strap may have a curved shape. A nonlinearity in a strap changes the position of the strap along the body of the wearer to provide enhanced comfort, increased support by the strap, and/or increased tension and support by the abdominal panel attached to the strap.

The maternity brace is fabricated from materials that are sufficiently durable to withstand the uses that have been described. The fabric is preferably smooth and comfortable to the touch, especially where it contacts the vulval region. The different components of the brace are preferably stitched together to improve the durability of the brace while minimizing costs associated with manufacturing the brace.

Although the preferred embodiments of the present invention have been disclosed for illustrative purposes, those who are skilled in the art will appreciate that various modifications, additions and substitutions are possible, without departing from the scope and spirit of the invention as set forth in the accompanying claims.

I claim:

1. A maternity brace for providing support to the vulval and abdominal regions, comprising:
    (a) a central fabric vulval panel for applying a supporting force to the vulval region, wherein the vulval panel is sized and shaped to engage the vaginal region without irritating the vagina;
    (b) a pair of fabric front straps attached to the vulval panel, wherein the front straps extend out from the vulval panel and away from each other;
    (c) a pair of fabric rear straps attached to the vulval panel, wherein the rear straps extend out from the vulval panel and away from each other;
    (d) a flexible adjusting belt in communication with the pair of front straps and the pair of rear straps; and
    (e) an abdominal panel positioned between the two front straps for applying a supporting force to the abdomen.

2. The maternity brace of claim 1, wherein the adjusting belt is sized and shaped to wrap around the body along the region of the upper abdomen.

3. The maternity brace of claim 1, wherein the abdominal panel is flexible.

4. The maternity brace of claim 3, wherein the abdominal panel is elastic and is stretchable in two dimensions.

5. The maternity brace of claim 1 further having connection means for removably and adjustably connecting the abdominal panel to each of the two front straps.

6. The maternity brace of claim 5, wherein the connection means comprise a hook and loop engagement assembly.

7. The maternity brace of claim 1, wherein the adjusting belt has locking means for opening and closing the adjusting belt.

8. The maternity brace of claim 7, wherein the adjusting belt has a front section and a back section and the locking means comprise a mechanical clasp in the front section of the adjusting belt.

9. The maternity brace of claim 1, wherein the two front straps are removably and adjustably attached to the adjusting belt by attachment means.

10. The maternity brace of claim 9, wherein the attachment means comprise a hook and loop engagement assembly.

11. The maternity brace of claim 9, wherein the two rear straps are removably attached to the adjusting belt.

12. The maternity brace of claim 11, wherein each of the two rear straps is sized and shaped to wrap around the adjusting belt and removably and adjustably attach to a front strap by coupling means.

13. The maternity brace of claim 12, wherein the coupling means comprise a hook and loop engagement assembly.

14. The maternity brace of claim 1 further having a back panel, wherein the adjusting belt has a front section and a back section and the back panel is fastened to the adjusting belt along the back section of the adjusting belt.

15. The maternity brace of claim 14 further having fastening means for removably and adjustably fastening the back panel to the adjusting belt.

16. The maternity brace of claim 15, wherein the fastening means comprise a hook and loop engagement assembly.

17. A maternity brace for providing support to the vulval region, comprising:
    (a) a central fabric vulval panel for applying a supporting force to the vulval region, wherein the vulval panel is sized and shaped to engage the vaginal region without irritating the vagina;
    (b) a pair of fabric front straps attached to the vulval panel, wherein the front straps extend out from the vulval panel and away from each other;
    (c) a pair of fabric rear straps attached to the vulval panel, wherein the rear straps extend out from the vulval panel and away from each other;
    (d) a flexible adjusting belt having a front section and a back section, wherein the adjusting belt is in communication with the pair of front straps and the pair of rear straps; and
    (e) a back panel fastened to the adjusting belt along the back section of the adjusting belt.

18. A maternity brace for providing support to the vulval and abdominal regions, comprising:
    (a) a central fabric vulval panel for applying a supporting force to the vulval region, wherein the vulval panel is sized and shaped to engage the vaginal region without irritating the vagina;
    (b) a fabric front strap attached to the vulval panel;
    (c) a fabric rear strap attached to the vulval panel;
    (d) a flexible adjusting belt in communication with the front strap and rear strap; and
    (e) an abdominal panel positioned proximate the front strap for applying a supporting force to the abdomen.

19. A maternity brace for providing support to the vulval region, comprising:
    (a) a central fabric vulval panel for applying a supporting force to the vulval region, wherein the vulval panel is sized and shaped to engage the vaginal region without irritating the vagina;
    (b) a pair of fabric front straps attached to the vulval panel, wherein the front straps extend out from the vulval panel and away from each other;
    (c) a pair of rear straps attached to the vulval panel, wherein the rear straps extend out from the vulval panel and away from each other, each of the two rear straps having a first segment and a second segment wherein the first segment is angularly displaced from the second segment; and
    (d) a flexible adjusting belt in communication with the pair of front straps and the pair of rear straps.

20. The maternity brace of claim 19, wherein each of the two front straps also has a first and second segment wherein the first segment is angularly displaced from the second segment.

* * * * *